United States Patent
Ecabert et al.

(10) Patent No.: US 11,185,372 B2
(45) Date of Patent: Nov. 30, 2021

(54) ASSISTING IN NAVIGATION OF A MEDICAL INSTRUMENT

(71) Applicants: Olivier Ecabert, Ebermannstadt (DE); Martin Hoheisel, Erlangen (DE)

(72) Inventors: Olivier Ecabert, Ebermannstadt (DE); Martin Hoheisel, Erlangen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 719 days.

(21) Appl. No.: 14/594,123

(22) Filed: Jan. 10, 2015

(65) Prior Publication Data

US 2015/0196368 A1 Jul. 16, 2015

(30) Foreign Application Priority Data

Jan. 10, 2014 (DE) .......................... 102014200326.1

(51) Int. Cl.
*A61B 34/20* (2016.01)
*A61B 8/12* (2006.01)
(Continued)

(52) U.S. Cl.
CPC ................ *A61B 34/20* (2016.02); *A61B 8/12* (2013.01); *A61B 17/00* (2013.01); *A61M 25/01* (2013.01);
(Continued)

(58) Field of Classification Search
CPC ...... A61M 25/00; A61B 2090/00; A61B 8/00; A61B 34/00; A61B 17/00; A61B 2034/00; A61B 2017/00; A61B 34/20; A61B 1/01
See application file for complete search history.

(56) References Cited

U.S. PATENT DOCUMENTS 5,125,410 A * 6/1992 Misono .................... A61B 8/06
128/908
5,373,845 A * 12/1994 Gardineer ................ A61B 8/12
600/445
(Continued)

FOREIGN PATENT DOCUMENTS

CN 101978243 A 2/2011
DE 102008054297 A1 5/2010
(Continued)

OTHER PUBLICATIONS

Gatzoulis, Loukianos, et al. "Three-dimensional forward-viewing intravascular ultrasound imaging of human arteries in vitro." Ultrasound in medicine & biology 27.7 (2001): 969-982. (Year: 2001).*
(Continued)

*Primary Examiner* — Sean D Mattson
(74) *Attorney, Agent, or Firm* — Lempia Summerfield Katz LLC

(57) ABSTRACT

A method for assisting in navigation of a medical instrument such as a catheter inside a hollow body such as a vascular system based on a dataset provided by a sensor device of the medical instrument is provided The method includes determining, by a control device, an internal extent of the hollow body based on the provided dataset and determining, by the control device, a navigation path for an impending movement of the medical instrument through the hollow body based on the determined internal extent. The control device is able to generate a control signal that describes a movement along the navigation path.

14 Claims, 2 Drawing Sheets

(51) Int. Cl.
*A61B 17/00* (2006.01)
*A61M 25/01* (2006.01)
*A61B 8/08* (2006.01)
*A61B 8/00* (2006.01)
*A61B 90/00* (2016.01)
*A61B 34/30* (2016.01)

(52) U.S. Cl.
CPC ............... *A61B 8/0891* (2013.01); *A61B 8/54* (2013.01); *A61B 2017/003* (2013.01); *A61B 2034/301* (2016.02); *A61B 2090/3735* (2016.02); *A61B 2090/3784* (2016.02)

(56) References Cited

U.S. PATENT DOCUMENTS

| | | | | | |
|---|---|---|---|---|---|
| 5,492,131 | A | * | 2/1996 | Galel | A61M 25/0105 600/114 |
| 5,638,819 | A | * | 6/1997 | Manwaring | A61B 1/0005 600/103 |
| 6,083,170 | A | * | 7/2000 | Ben-Haim | A61B 5/0422 600/462 |
| 8,491,484 | B2 | * | 7/2013 | Lewis | A61B 5/6851 600/459 |
| 2005/0288577 | A1 | * | 12/2005 | Weese | G06T 19/00 600/434 |
| 2006/0036167 | A1 | * | 2/2006 | Shina | A61B 6/12 600/433 |
| 2006/0074297 | A1 | * | 4/2006 | Viswanathan | A61B 34/73 600/424 |
| 2006/0241465 | A1 | * | 10/2006 | Huennekens | A61B 6/504 600/458 |
| 2007/0016068 | A1 | * | 1/2007 | Grunwald | A61B 8/488 600/468 |
| 2007/0055128 | A1 | * | 3/2007 | Glossop | A61B 1/018 600/407 |
| 2007/0268287 | A1 | * | 11/2007 | Magnin | A61B 5/0062 345/419 |
| 2008/0154137 | A1 | * | 6/2008 | Pruvot | G06T 7/136 600/467 |
| 2009/0247863 | A1 | | 10/2009 | Proulx et al. | |
| 2010/0113919 | A1 | * | 5/2010 | Maschke | A61B 17/221 600/424 |
| 2010/0280320 | A1 | * | 11/2010 | Alvarez | A61B 17/00234 600/146 |
| 2011/0230758 | A1 | * | 9/2011 | Eichler | A61B 5/06 600/424 |
| 2012/0046521 | A1 | * | 2/2012 | Hunter | A61B 5/062 600/104 |
| 2012/0059253 | A1 | * | 3/2012 | Wang | A61B 6/00 600/427 |
| 2013/0109958 | A1 | | 5/2013 | Baumgart et al. | |
| 2013/0204138 | A1 | * | 8/2013 | Belohlavek | A61B 34/20 600/453 |
| 2013/0223702 | A1 | * | 8/2013 | Holsing | A61B 8/0841 382/128 |
| 2013/0303910 | A1 | * | 11/2013 | Hubbard | A61B 8/06 600/443 |

FOREIGN PATENT DOCUMENTS

| | | |
|---|---|---|
| WO | WO2011134083 A1 | 11/2011 |
| WO | WO2013029644 A1 | 3/2013 |

OTHER PUBLICATIONS

Park, Jun Woo, et al. "Haptic virtual fixture for robotic cardiac catheter navigation." Artificial organs 35.11 (2011): 1127-1131. (Year: 2011).*

German Office Action for German Application No. 10 2014 200 326.1, dated Oct. 10, 2014, with English Translation.

Technology Advantages and System Overview, The Sensei Robotic Catheter System, Hansen Medical, http://www.hansenmedical.com/advantages.aspx, http://www.hansenmedical.com/system.aspx, Dec. 19, 2006.

Chinese Office Action and Search Report for Chinese Patent Application No. 201510052928.9, dated Sep. 30, 2016, with English Translation.

* cited by examiner

ASSISTING IN NAVIGATION OF A MEDICAL INSTRUMENT

This application claims the benefit of DE 10 2014 200 326.1, filed on Jan. 10, 2014, which is hereby incorporated by reference in its entirety.

BACKGROUND

The present embodiments relate to assisting in navigation of a medical instrument inside a hollow body based on a dataset provided by a sensor device of the medical instrument.

Robotically steerable catheter systems may be employed in electrophysiology (e.g., in the Sensei X system from Hansen Medical, Inc., Mountain View, Calif.) in order to carry out examinations of a hollow body organ (e.g., to conduct an intravascular examination). A force with which, for example, a catheter presses against a vessel wall is determined in the process. In the event of a pressure against a vessel wall, the catheter is to be steered away from the vessel wall in order to minimize any trauma to the vessel wall. This also provides that a force that is exerted on the catheter may not always be utilized to control advancement of the catheter.

In known methods, the catheter is advanced so carefully that any trauma to the vessel wall is avoided. Alternatively, the centerline may be calculated from an angiographic image previously acquired with use of contrast agent. Due to patient movements, however, the centerline calculated in this way no longer coincides exactly with the centerline during the intervention.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a force being exerted by a medical instrument on a hollow body at the time of an impending movement of the medical instrument may be avoided.

One or more of the present embodiments are based on the idea of determining an internal extent of the hollow body by a sensor device that is arranged on the medical instrument and by a control device. On the basis thereof, a navigation path for the medical instrument may be established. By this, an exertion of force by the medical instrument on an internal wall of the hollow body and the probability of a trauma to the internal wall are reduced or even avoided entirely.

One or more methods of the present embodiments accordingly serve to assist in navigation of a medical instrument (e.g., a catheter) inside a hollow body based on a dataset provided by a sensor device of the medical instrument (e.g., a provided dataset). The hollow body may include, for example, at least part of an animal or human vascular system. The sensor device includes at least one sensor (e.g., an ultrasound sensor).

The method according to one or more of the present embodiments is characterized by the acts performed by a control device of: determining an internal extent of the hollow body based on the provided dataset; and determining a navigation path for an impending movement of the medical instrument through the hollow body based on the determined internal extent.

In this context, a control device includes a control unit or an equipment component that is configured for electronic data processing and is able to control an electronic medical apparatus such as, for example, a catheter or a cannula. An internal extent encompasses, for example, an internal dimension, a geometry, a lattice model and/or a shape of an internal wall of the hollow body. The determined navigation path based thereon describes a direction of movement for the medical instrument along which a maximally collision-free guidance of the medical instrument may be provided.

The method according to one or more of the present embodiments enables a navigation path to be determined and corrected for an impending movement and/or guidance of the medical instrument in the hollow body, even when the latter does not extend in a rectilinear manner. The method is suitable, for example, for navigating and/or guiding a medical instrument (e.g., inside a human or animal hollow body such as a vascular system or an intestinal system). The method is also suitable, for example, for navigation and/or guidance inside a further hollow medical instrument (e.g., for cleaning or inspecting an internal wall of a cannula). The method allows a movement of the medical instrument inside the hollow body that is to the greatest possible extent free of collisions and contactless, such that an application of force or damage to the internal wall of the hollow body is reduced or even avoided altogether. A force may be exerted simultaneously on the medical instrument and utilized for the advancement of the medical instrument.

In addition, the internal wall is, for example, recessed or protuberant in shape. The medical instrument may nonetheless have a greatest possible clearance with respect to all sides of the internal wall, and the position of the medical instrument may be corrected in the best possible way. For this reason, in a further embodiment, a relative position of the medical instrument in relation to the hollow body is determined by the control device based on the dataset. The navigation path is determined based on the relative position of the medical instrument.

According to a further embodiment, a control signal may be generated by the control device for the purpose of at least partially or completely adapting a shape of the medical instrument to a topography of the hollow body. Thus, for example, a proximal end of the medical instrument may be guided, for example, by a flexing or bending action around a curve in the hollow body, and in this way, a contact with the internal wall may be reduced or completely avoided.

Alternatively or in addition, a control signal may be generated by the control device for the purpose of shaping the medical instrument with point-by-point accuracy to match a profile of the hollow body. In this case, for example, a wand-shaped medical instrument is adapted in part or over an entire length (e.g., from end to end) to match the hollow body profile. This facilitates a maximally contactless guidance of the medical instrument over a major portion of the internal wall.

According to one embodiment, the control device generates a control signal that describes a movement along the navigation path. This enables a robot-controlled guidance of the medical instrument. The exertion of force may be utilized for the most part for advancement.

According to one embodiment, the control device may determine a distance of the medical instrument from an internal wall of the hollow body based on the dataset. The determined navigation path lies inside a specified region at a specified minimum distance from the internal wall. The specified region may be determined, for example, using a specified tolerance range around, for example, a center of the hollow body. In one embodiment, the navigation path lies on a center of the hollow body (e.g., about the point that is as far as possible at an equally great distance from all sides of the internal wall). In other words, the control device may determine, for example, a diameter of the hollow body and define a center point as the navigation point. The sequence of the center points over the course of the hollow body yields the navigation path.

In addition to the guiding of the medical instrument, in order to also enable an operator to conduct an examination of a specified site of interest on the internal wall of the hollow body (e.g., a plaque in a blood vessel wall), a further embodiment of the method is characterized in that the control device determines a distance of the medical instrument from the specified site of the internal wall of the hollow body, and the determined navigation path leads to the specified site.

The dataset may be provided by a sonographic sensor (e.g., an IVUS sensor). In contrast to optical sensors, no light and no use of a contrast agent are then required for the acquisition of the dataset. As a result, the dataset delivers a much more accurate image. The medical instrument may include a catheter.

In one embodiment, a control device that is configured to perform the method acts relevant to the control device according to the above-described embodiments is provided.

In one embodiment, a medical apparatus including a medical instrument (e.g., a catheter) and a control device is provided. In one embodiment, the medical apparatus also includes a sensor device (e.g., a sonographic sensor device).

BRIEF DESCRIPTION OF THE DRAWINGS

Functionally same elements are designated by the same reference signs in the figures, in which.

DETAILED DESCRIPTION

Figure 1:
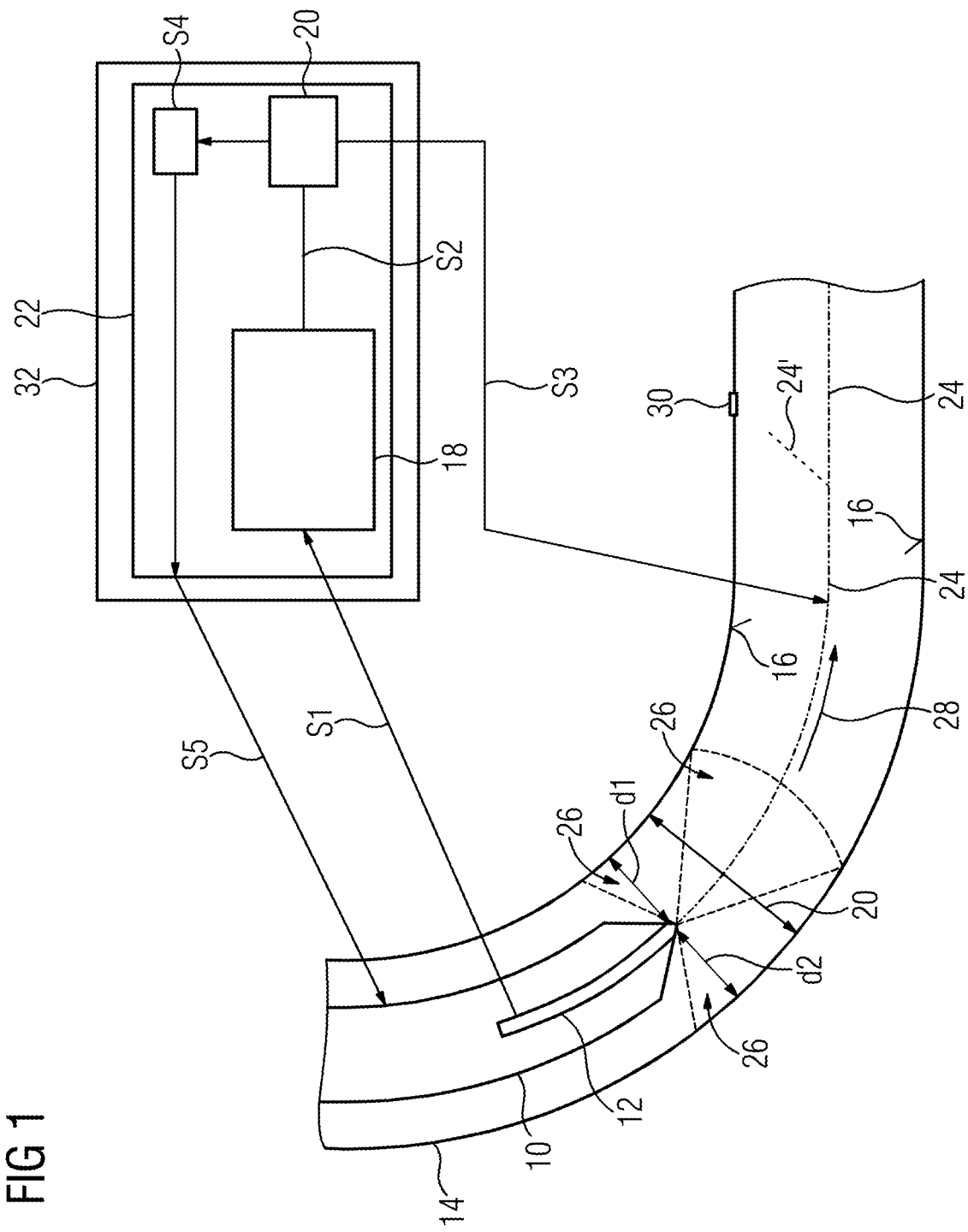
FIG. 1 is a schematic representation of the principle according to the method of one embodiment.

FIG. 1 illustrates the principle of the method according to one or more of the present embodiments. In this case, FIG. 1 shows an exemplary medical instrument 10 that includes a sensor device 12. In the present example, the medical instrument 10 includes, for example, a catheter or a cannula that may be inserted in, for example, a blood vessel as hollow body 14. Alternatively, the medical instrument 10 may also include, for example, a tool, for example, for cleaning or inspecting a tube as hollow body 14. The method according to one or more of the present embodiments provides a method for moving the medical instrument 10 virtually contactlessly through a curved or recessed or protuberant hollow body 14. In this regard, a curved hollow body 14 is shown in FIG. 1 as an exemplary case (e.g., a sub-branch of a vascular system). Contact with and/or damage or trauma to an internal wall 16 of the hollow body 14 is dramatically reduced by the method according to one or more of the present embodiments.

The sensor device 12 is configured to generate a dataset 18 (e.g., an image dataset) that replicates, for example, an image of the internal wall 16 of the hollow body 14. The sensor device 12 may be arranged at an extension end of the medical instrument 10 (e.g., at a proximal tip of a medical instrument 10 embodied as a sheath or wand). However, for example, a lateral arrangement of the sensor device 12 may also be provided. The arrangements cited by way of example are known from the prior art.

The sensor device 12 may include, for example, an optical sensor (e.g., a sensor for optical coherence tomography). The internal extent 20 of the hollow body 14 may be determined, for example, by way of an optical distance measurement.

According to an alternative, the sensor device 12 includes one or more probes (not shown in FIG. 1) that detect a restoring force and/or a change in angle of the probe or probes relative to an axis of the medical instrument 10 when the at least one probe touches the internal wall 16. The effect of a force exerted by such an exemplary probe on the internal wall 16 is significantly smaller than the force exerted in the case of a conventional method using a conventional medical instrument 10.

In one embodiment, the sensor device 12 includes (as shown in FIG. 1) a sonographic sensor (e.g., an echo sounder or an intravascular ultrasound sensor (IVUS)) as is known from the prior art. In this case, the dataset 18 may be generated, and the internal extent 20 of the hollow body 14 is determined, for example, by way of a time-of-flight measurement and/or by way of an amplification of a Doppler effect.

The dataset 18 of the sensor device 12 is provided to a control device 22 (e.g., a control unit or a microcontroller of a computer terminal (method act S1)). The control device may, for example, be connected to the medical instrument 12 via a wireless data communications link over, for example, WLAN, or has a wired data communications link.

The control device 22 segments the image of the dataset 18 such that the internal extent 20 of the hollow body 14 (e.g., the shape of the internal wall 16) may be determined automatically. As a result of the segmentation, the individual pixels are assigned to details of the image (e.g., a vessel wall or the medical instrument 10). According to one or more of the present embodiments, the internal extent 20 (S2) is also determined by the control device 22. An algorithm accessible in a known manner may be used for this purpose.

Figure 2:
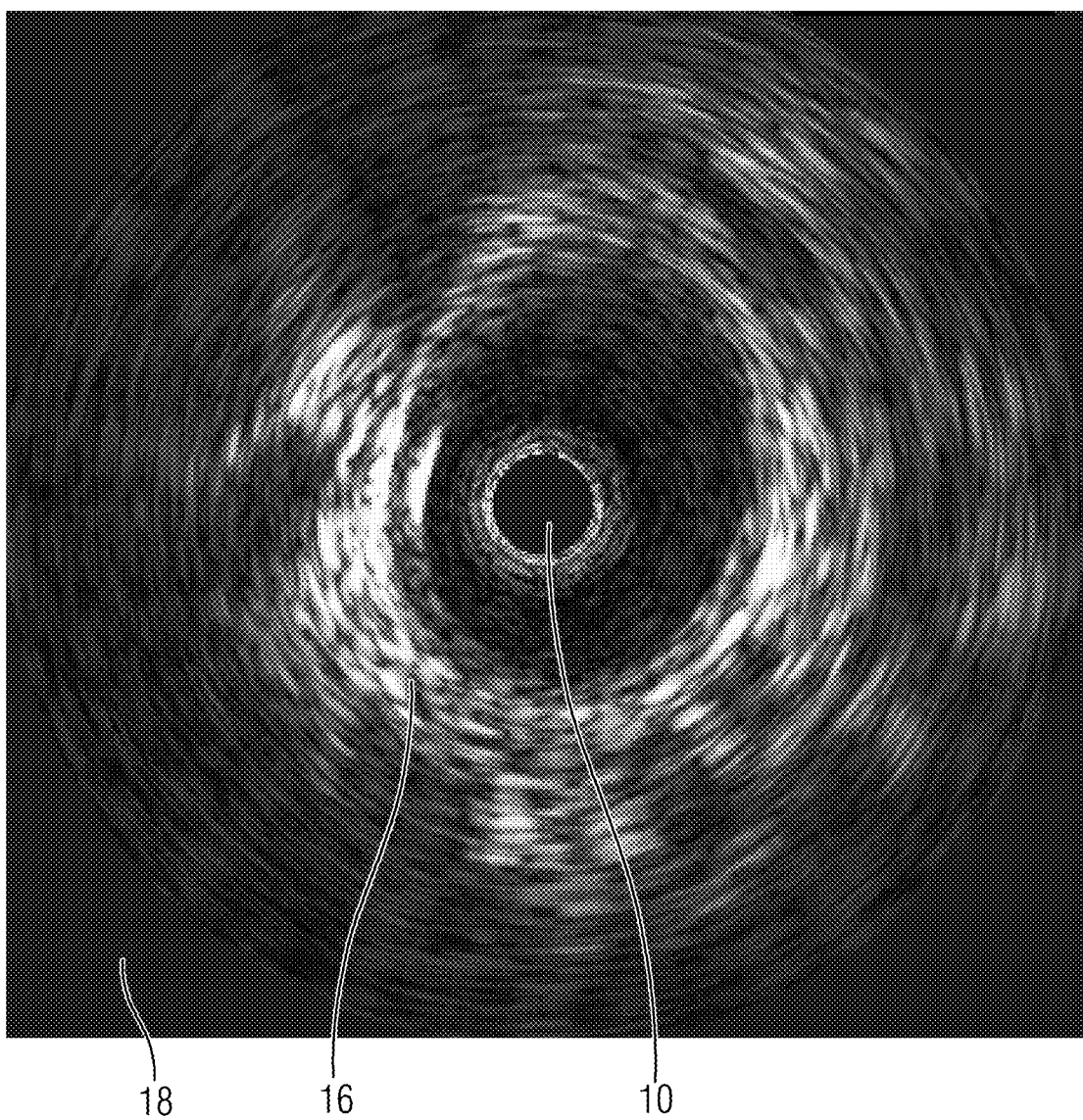
FIG. 2 is a schematic representation of an image from a sensor device according to another embodiment.

In the dataset 18 generated by the sensor device 12 (e.g., an image) of the hollow body 14, the internal wall 16 of the hollow body and the medical instrument 10, for example, may be clearly visible (see FIG. 2). In the example shown in FIG. 2, the image is, for example, a sonogram of the exemplary sensor device 12. In this case, in the example shown in FIG. 2, the medical instrument 10 is located, for example, not in the center of the hollow body 14, but close to an exemplary vessel wall.

In the present example, the control device 22 determines, for example, at least one distance d1, d2 of the medical instrument 10 from the internal wall 16. The regions 26 delimited by dashed lines in FIG. 2 represent exemplary regions 26 detected by the sensor device 12 (e.g., at least one region 26 to the side of the medical instrument 10 or a cone-shaped region 26 located ahead of the medical instrument 10 in the planned movement direction 28).

From the exemplary distances d1, d2, the control device 22 determines, for example, a diameter of the hollow body 14 as an internal dimension (e.g., as internal extent 20 (S2); a diameter of 2 centimeters at a first distance d1 of the medical instrument 10 of 0.5 centimeters from the internal wall 16, and a further distance d2 of 1.5 centimeters). The determined navigation path 24 lies, for example, on a centerline of the internal extent 20 (e.g., in each case, at a distance of one centimeter from the internal wall 16). In this instance, the navigation path 24 is depicted in FIG. 1 drawn as a dash-dotted line. In one embodiment, a predetermined tolerance range may be taken into account. In the present example, the distances d1, d2 from the internal wall 16 are equal, for example, to 0.5 centimeters and 1.5 centimeters. Consequently, the medical instrument 10 is not located in the center of the internal extent 20, and it is necessary to correct the position of the medical instrument 10.

Optionally, a position of the medical instrument 10 may be determined. This enables an advancement of the medical instrument 10 to be controlled such that the medical instrument 10 moves along the determined navigation path 24 (e.g., along a centerline of the hollow body 14 as navigation path 24) at all times.

In one embodiment, using a method of the kind to identify, for example, a site of interest 30 on the internal wall 16 of the hollow body 14 based on the image 18 acquired by the sensor device 12, the site may be specified and/or the site may be steered toward in a targeted manner by the, for example, robotically controlled medical instrument 10. The control device 22 determines a distance of the medical instrument 10 from a specified site 30 on an internal wall 16 of the hollow body 14. The determined navigation path 24' (shown as a dotted line) leads to the specified site 30 (e.g., a plaque in the exemplary blood vessel or a porous site in a tube as hollow body 14).

A control signal that describes a movement along the navigation path 24 may be generated (S4) by the control device 22. The control signal may be transmitted to the medical instrument 10 via a wireless or wired data communications link. The control signal may specify, for example, a force and/or a direction in which the medical instrument 10 is moved by, for example, a motor of the medical instrument 10.

Alternatively or in addition, a control signal may be generated by the control device 22 for the purpose of adapting a shape of the medical instrument 10 and/or of shaping the medical instrument 10 with point-by-point accuracy to match a profile of the hollow body 14. If the medical instrument 10 is embodied, for example, as a sheath having a plurality of segments, the plurality of segments may be, for example, moved relative to one another by the control signal such that the medical instrument 10 adapts itself to match an overall profile of the hollow body 14. Equally, for example, a proximal tip of the exemplary catheter may be curved along the navigation path 24.

The medical apparatus 32 shown in FIG. 1 (e.g., a control console for a catheter) includes the control device 22 and in addition may also include the medical instrument 10.

The above-described exemplary embodiment illustrates the idea of arranging a sensor device 12 (e.g., an intravascular ultrasound sensor ("IVUS sensor")) at, for example, a tip of a medical instrument 10 (e.g., a catheter). An image 18 from the sensor device 12 (e.g., an IVUS image) enables an internal wall 16 of a hollow body 14 (e.g., a vessel wall) and/or a position of the medical instrument 10 in the hollow body 14 to be visualized. The advancement of the medical instrument 10 may be controlled such that the medical instrument 10 may always move in the center of the hollow body 14.

In one embodiment, for example, a robotically controlled medical instrument 10 may be equipped with a sensor device 12 (e.g., an IVUS sensor). This enables the medical instrument 10 to be navigated, for example, along the center of the hollow body 14 without any need for the medical instrument 10 to come into contact with the hollow body 14. Consequently, a force may be exerted onto the internal wall 16 of the hollow body 14. As a result, the risk of an undesirable perforation of the internal wall 16 of the hollow body 14 is considerably reduced.

For example, sites of interest 30 on the internal wall 16 of the hollow body 14 may be identified in the image generated by the sensor device, and the medical instrument 10 may be moved in a targeted manner toward the sites.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for assisting in navigation of a medical instrument inside a hollow body based on a dataset provided by a sensor device of the medical instrument, the method comprising:
   generating, by the sensor device, an image of the hollow body based on the provided dataset;
   determining, by a control device, an internal extent of the hollow body based on measurements of the hollow body by the sensor device or by segmenting the generated image, wherein the internal extent is an internal measurement or shape of the hollow body;
   determining, by the control device, a navigation path through the hollow body for an impending movement of the medical instrument inside the hollow body as a function of the determined internal extent, wherein determining the navigation path comprises: (a) determining, based on the determined internal extent, a centerline of the internal extent of the hollow body, (b) determining a specified region around the centerline of the internal extent based on a predetermined tolerance range and the dataset provided by the sensor, (c) determining, by the control device, a relative position of the medical instrument in relation to the hollow body and the specified region based on the dataset, and (d) determining the navigation path based on the relative position of the medical instrument and the specified region around the centerline of the internal extent;
   generating, by the control device, a control signal for guidance of the medical instrument based on the determined navigation path, the control signal describing the impending movement of the medical instrument along the navigation path; and
   controlling, by the control device, the medical instrument with the control signal.

2. The method of claim 1, further comprising:
   generating, by the control device, another control signal to at least partly adapt a shape of the medical instrument to match a profile of the hollow body.

3. The method of claim 1, further comprising:
generating, by the control device, another control signal to shape the medical instrument to match a profile of the hollow body.

4. The method of claim 1, further comprising:
determining, by the control device, a distance of the medical instrument from an internal wall of the hollow body based on the dataset,
wherein the determined navigation path lies inside the specified region at a specified minimum distance from the internal wall.

5. The method of claim 1, further comprising:
determining, by the control device, a distance of the medical instrument from a specified site on an internal wall of the hollow body,
wherein the determined navigation path leads to the specified site.

6. The method of claim 1, wherein the dataset is provided by the sensor device, the sensor device comprising a sonographic sensor.

7. The method of claim 6, wherein the sonographic sensor comprises an intravascular ultrasound (IVUS) sensor.

8. The method of claim 1, wherein the medical instrument comprises a catheter.

9. The method of claim 1, further comprising:
repeating the determining of the internal extent, the determining of the navigation path, the generating of the control signal, and the controlling of the medical instrument sequentially as the medical instrument moves along the inside of the hollow body.

10. A control device comprising:
a processor configured to assist in navigation of a medical instrument inside a hollow body based on a dataset provided by a sensor device of the medical instrument, the processor further configured to:
determine an internal extent of the hollow body based on measurements of the hollow body by the sensor device, wherein the internal extent is an internal measurement or shape of the hollow body, the determination of the internal extent comprising measurement of a distance of the medical instrument from an internal wall of the hollow body;
determine a navigation path through the hollow body for an impending movement of the medical instrument inside the hollow body based on the determined internal extent, wherein the determination of the navigation path comprises: (a) determination, based on the determined internal extent, of a centerline of the internal extent of the hollow body, (b) determination of a specified region around the centerline of the internal extent based on a predetermined tolerance range and the dataset provided by the sensor device, (c) determination of a relative position of the medical instrument in relation to the hollow body and the specified region based on the dataset, and (d) determination of the navigation path based on the relative position of the medical instrument and the specified region around the centerline of the internal extent;
generate a control signal for guidance of the medical instrument based on the determined navigation path, the control signal describing the impending movement of the medical instrument along the navigation path; and
control the medical instrument with the control signal.

11. A medical apparatus comprising:
a medical instrument comprising a sensor device; and
a controller configured to assist in navigation of the medical instrument inside a hollow body based on a dataset provided by the sensor device, the controller further configured to:
determine an internal extent of the hollow body based on measurements of the hollow body or by segmentation of an image of the hollow body, the image of the hollow body being based on the provided dataset, wherein the internal extent is an internal measurement or shape of the hollow body;
determine a navigation path through the hollow body for an impending movement of the medical instrument inside the hollow body as a function of the determined internal extent, wherein the determination of the navigation path comprises:
(a) determination, based on the determined internal extent, of a centerline of the internal extent of the hollow body, (b) determination of a specified region around the centerline of the internal extent based on a predetermined tolerance range and the dataset provided by the sensor device, (c) determination of a relative position of the medical instrument in relation to the hollow body and the specified region based on the dataset, and (d) determination of the navigation path based on the relative position of the medical instrument and the specified region around the centerline of the internal extent;
generate a control signal for guidance of the medical instrument based on the determined navigation path, the control signal describing the impending movement of the medical instrument along the navigation path; and
control the medical instrument with the control signal.

12. The medical apparatus of claim 11, wherein the sensor device comprises a sonographic sensor device.

13. The medical apparatus of claim 11, wherein the controller is configured to generate another control signal to at least partly adapt a shape of the medical instrument to match a profile of the hollow body.

14. The medical apparatus of claim 11, wherein the controller is configured to generate another control signal to shape the medical instrument to match a profile of the hollow body.

* * * * *